United States Patent
Yoshida

(10) Patent No.: US 10,592,815 B2
(45) Date of Patent: Mar. 17, 2020

(54) CALCULATION APPARATUS, CALCULATION METHOD, AND PROGRAM

(71) Applicant: NEC Corporation, Minato-ku, Tokyo (JP)

(72) Inventor: Arihiro Yoshida, Tokyo (JP)

(73) Assignee: NEC CORPORATION, Tokyo (JP)

( * ) Notice: Subject to any disclaimer, the term of this patent is extended or adjusted under 35 U.S.C. 154(b) by 99 days.

(21) Appl. No.: 15/911,503

(22) Filed: Mar. 5, 2018

(65) Prior Publication Data
US 2018/0268316 A1    Sep. 20, 2018

(30) Foreign Application Priority Data

Mar. 15, 2017   (JP) .................. 2017-049681

(51) Int. Cl.
| | |
|---|---|
| G06F 15/76 | (2006.01) |
| G06N 10/00 | (2019.01) |
| B82Y 10/00 | (2011.01) |
| G16C 10/00 | (2019.01) |
| G06F 15/80 | (2006.01) |

(52) U.S. Cl.
CPC .............. *G06N 10/00* (2019.01); *B82Y 10/00* (2013.01); *G06F 15/76* (2013.01); *G16C 10/00* (2019.02); *G06F 15/80* (2013.01)

(58) Field of Classification Search
CPC ........ G06N 10/00; G16C 10/00; B82Y 10/00; G06F 15/76
See application file for complete search history.

(56) References Cited

U.S. PATENT DOCUMENTS

| | | |
|---|---|---|
| 2005/0027458 A1 | 2/2005 | Merz, Jr. et al. |
| 2012/0150512 A1 | 6/2012 | Takai |

FOREIGN PATENT DOCUMENTS

| | | |
|---|---|---|
| JP | 2003-012567 A | 1/2003 |
| JP | 2008-021259 A | 1/2008 |
| JP | 2013-156796 A | 8/2013 |
| WO | 2011/021279 A1 | 2/2011 |

OTHER PUBLICATIONS

Kobayashi, "Divide the difficulties!—Challenge to the efficiency and refinement of quantum chemical computation using computer . . . ", Waseda Institute for Advanced Study (WIAS), Jul. 2012. (Year: 2012).*

Kazuo Kitaura et al., "Fragment molecular orbital method: an approximate computational method for large molecules", Chemical Physics Letters 313, pp. 701-706, Nov. 12, 1999, Elsevier, Netherlands.

(Continued)

*Primary Examiner* — Tan V Mai

(57) ABSTRACT

A calculation apparatus has: a dividing unit configured to divide a predetermined space including a substance of a calculation target into a plurality of regions; an electron wave function calculating unit configured to calculate an electron wave function for each of the regions obtained by the dividing by the dividing unit; and an all-electron wave function calculating unit configured to calculate an all-electron wave function by multiplying electron wave functions of the respective regions calculated by the electron wave function calculating unit.

20 Claims, 8 Drawing Sheets

(56) References Cited

OTHER PUBLICATIONS

Weitao Yang, "Direct Calculation of Electron Density in Density-Functional Theory", Physical Review Letters, vol. 66, No. 11, pp. 1438-1441, Mar. 18, 1991.
Aoyama et al., "Break Difficulties!—Challenge to Efficiency Improvement and Refinement of Quantum Chemistry Calculation Using Computer, Masato Kobayashi, Assistant Processor", Online Document of Waseda Institute for Advanced Study, Jul. 2012, URL: https://www.waseda.jp/inst/wias/news/2012/07/11/2984/, cited in JPOA.
Kobayashi, "O(N)Electronic State Calculation and MD Simulation by Divide-And-Conquer (DC) Method", Ensemble (news letter) of Molecular Simulation Society of Japan, Apr. 2016, pp. 90-94, vol. 18 No. 2, cited in JPOA.
Japanese Office Action for JP Application No. 2017-049681 dated Mar. 6, 2018 with English Translation.

\* cited by examiner

1 QUANTUM CHEMISTRY CALCULATION APPARATUS

CALCULATION APPARATUS, CALCULATION METHOD, AND PROGRAM

INCORPORATION BY REFERENCE

This application is based upon and claims the benefit of priority from Japanese patent application No. 2017-049681, filed on Mar. 15, 2017, the disclosure of which is incorporated herein in its entirety by reference.

TECHNICAL FIELD

The present invention relates to a calculation apparatus, a calculation method, and a program. More specifically, the present invention relates to a calculation apparatus that calculates an all-electron wave function, a calculation method, and a program.

BACKGROUND ART

Quantum chemistry calculation using a calculator such as an arithmetic device is known.

For example, Patent Document 1 discloses a quantum state estimation method for estimating the quantum state of an atom or a molecule at high speeds. To be specific, according to Patent Document 1, by a computer program, a control/arithmetic unit divides a space in or near a substance into a plurality of three-dimensional regions (cells), assigns a normal distribution function to each of the cells, and sets it as a basis function. Further, by performing discrete Fourier transform of the potential energy of atoms or molecules mapped to the space, and thereafter, moving data of the rear half of a discrete Fourier transform data sequence arranged in each basic reciprocal lattice direction to the front of data of the front half of the data sequence, discrete Fourier transform shift data is obtained. After that, a Hamiltonian matrix and an overlap integral matrix for solving a Schrödinger equation by a numerical variation method are calculated by merely substituting the basis function and the discrete Fourier transform shift data to an analytic expression. Then, by solving a secular equation from the Hamiltonian matrix and the overlap integral matrix to obtain unique energy, a wave function is calculated. As a result, various useful physical quantities are calculated.

Further, for example, Patent Document 2 is a related technique. Patent Document 2 discloses a parallel synthesis method for efficient electronic state calculation of a macromolecule. To be specific, according to Patent Document 2, a macromolecule is divided into segments with a length or more at which a localized molecular orbital (LMO) can be constructed and with the number of atoms or less that can be calculated by a well-known electronic state calculation method. Then, only an active LMO is extracted and, the atomic orbital of a terminal part away from an interaction part in the active LMO is removed and, by using the result as a calculation target, the electronic state of the entire macromolecule is solved as an eigenvalue problem based on a localized molecular orbital localized to a part strongly interacting with the coupling of the segments. Such a configuration can increase the efficiency of calculation.

Further, for example, Patent Document 3 is a related technique. Patent Document 3 discloses a method of, in order to apply a divide-and-conquer method to quantum chemistry calculation that needs global calculation, using the electron density (density matrix) of a fragmented molecular chain to find energy by many-body expansion Further, for example, Patent Document 4 is a related technique. Patent Document 4 discloses a method of, in order to apply a divide-and-conquer method to quantum chemistry calculation that needs global calculation, using the electron density (density matrix) of a fragmented molecular chain and, in the calculation, building a buffer region in the surroundings to incorporate an effect of the environment.

Patent Document 1: Japanese Unexamined Patent Application Publication No. JP-A 2013-156796
Patent Document 2: Japanese Unexamined Patent Application Publication No. JP-A 2003-012567
Non-Patent Document 1: Chemical Physics Letters, issued on Nov. 12, 1999, vol. 313, pp. 701-706
Non-Patent Document 2: Physical Review Letters, issued on Mar. 18, 1991, vol. 66, pp. 1438-1441

In quantum chemistry, one of the calculation targets is an all-electron wave function. There has been a problem that as a molecular system that is a calculation target becomes large scale, finding an all-electron wave function requires very large order computational complexity and main memory usage. This is because, for example, calculation and storage of two-electron integrals are required in the calculation process, the number thereof is the order of the fourth power of the number of one-electron basis functions and, in the high-precision calculation, the number of multi-electron basis functions required according to approximation accuracy is on the order of 5 to 7 or more of the number of electrons and one-electron basis functions.

On the other hand, the technique according to Cited Document 1 is a technique for high-speed estimation of the quantum state of an atom and a molecule, and it cannot be applied to calculation of an all-electron wave function. Moreover, the technique according to Cited Document 2 enables calculation of electronic density and energy, but it does not enable an all-electron wave function.

Further, in order to calculate an all-electron wave function by using the techniques of Cited Documents 3 and 4, an extended method of Cited Documents 3 and 4 is used. In a case where such an extended method is used, it requires computational complexity and main memory usage of extraordinary order that is equivalent to the conventional method as a molecular system becomes large scale.

Thus, it has been difficult to solve a problem that it is difficult to suppress computational complexity in calculation of an all-electron wave function.

SUMMARY OF THE INVENTION

Accordingly, an object of the present invention is to provide a calculation apparatus that solves the problem that it is difficult to suppress computational complexity in calculation of an all-electron wave function, a calculation method, and a program.

In order to achieve the object, a calculation apparatus as an aspect of the present invention includes: a dividing unit configured to divide a predetermined space including a substance of a calculation target into a plurality of regions; an electron wave function calculating unit configured to calculate an electron wave function for each of the regions obtained by the dividing by the dividing unit; and an all-electron wave function calculating unit configured to calculate an all-electron wave function by multiplying electron wave functions of the respective regions calculated by the electron wave function calculating unit.

Further, a calculation method as another aspect of the present invention is executed by an information processing apparatus and includes: dividing a predetermined space including a substance of a calculation target into a plurality of regions; calculating an electron wave function for each of the regions obtained by the dividing; and calculating an all-electron wave function by multiplying calculated electron wave functions of the respective regions.

Further, non-transitory computer-readable medium storing a program as another aspect of the present invention is a non-transitory computer-readable medium storing a program including instructions for causing an information processing apparatus to realize: a dividing unit configured to divide a predetermined space including a substance of a calculation target into a plurality of regions; an electron wave function calculating unit configured to calculate an electron wave function for each of the regions obtained by the dividing by the dividing unit; and an all-electron wave function calculating unit configured to calculate an all-electron wave function by multiplying electron wave functions of the respective regions calculated by the electron wave function calculating unit.

With the configurations as described above, the present invention can provide a calculation apparatus which solves the problem that it is difficult to suppress computational complexity in calculation of an all-electron wave function, a calculation method, and a program.

EXEMPLARY EMBODIMENT

First Exemplary Embodiment

Figure 1:
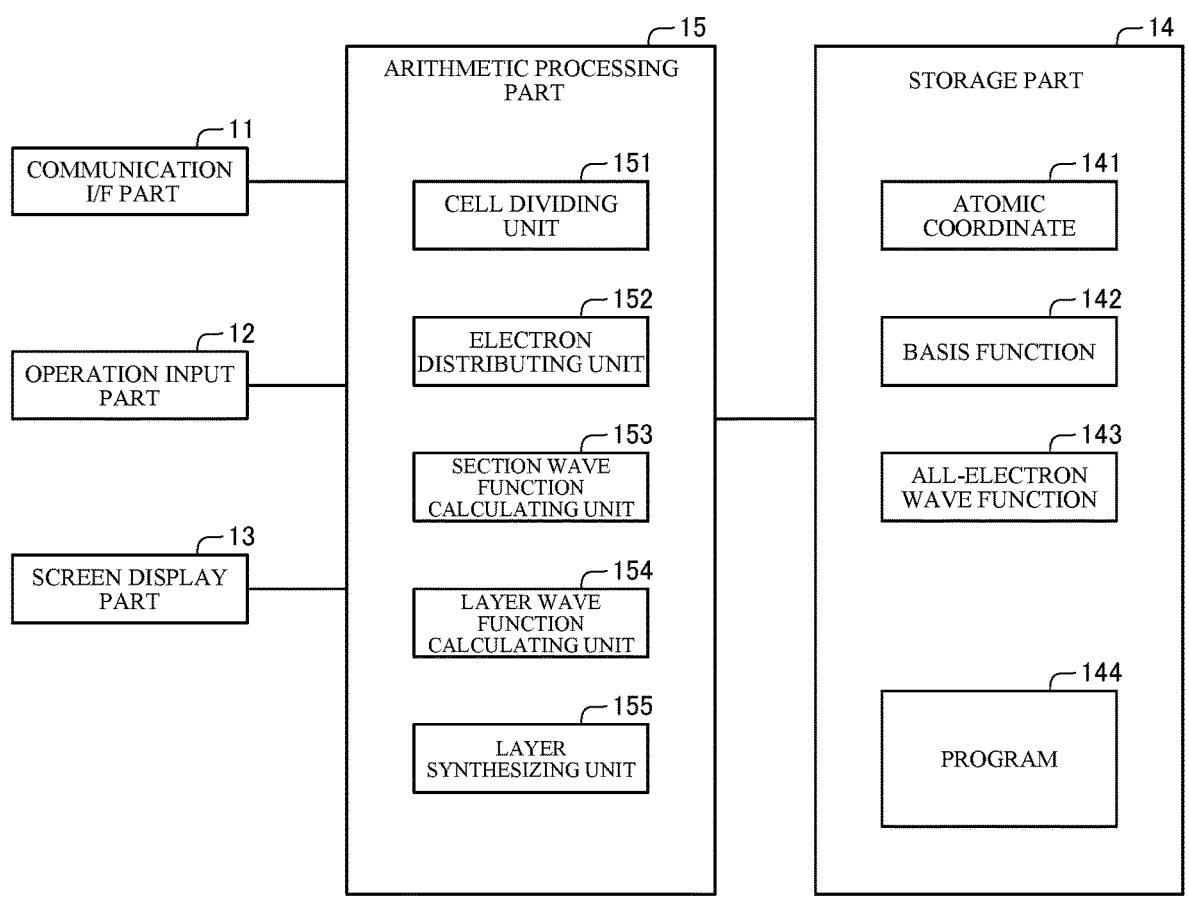
FIG. 1 is a block diagram showing an example of a configuration of a quantum chemistry calculation apparatus according to a first exemplary embodiment of the present invention.
Figure 2:
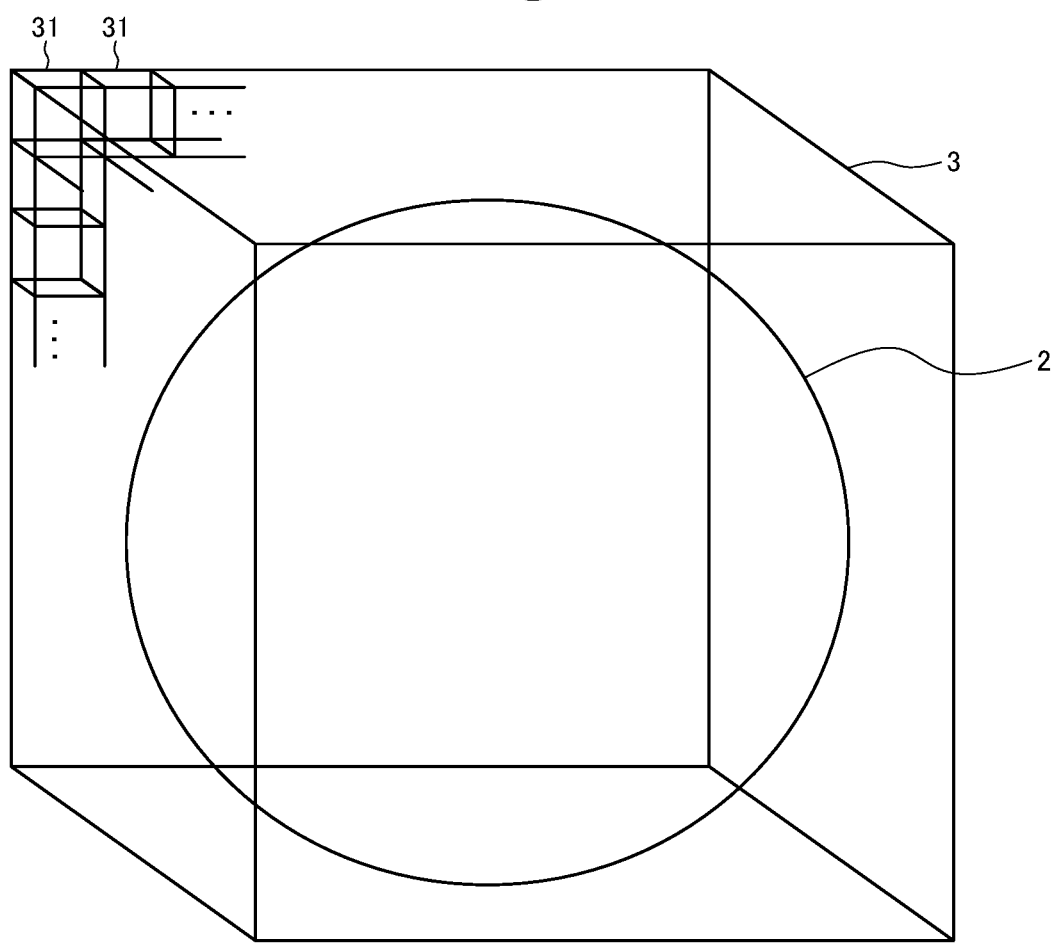
FIG. 2 is a diagram showing an example of dividing a space including a system (a molecular system, a crystal system, and the like) into cells.
Figure 3:
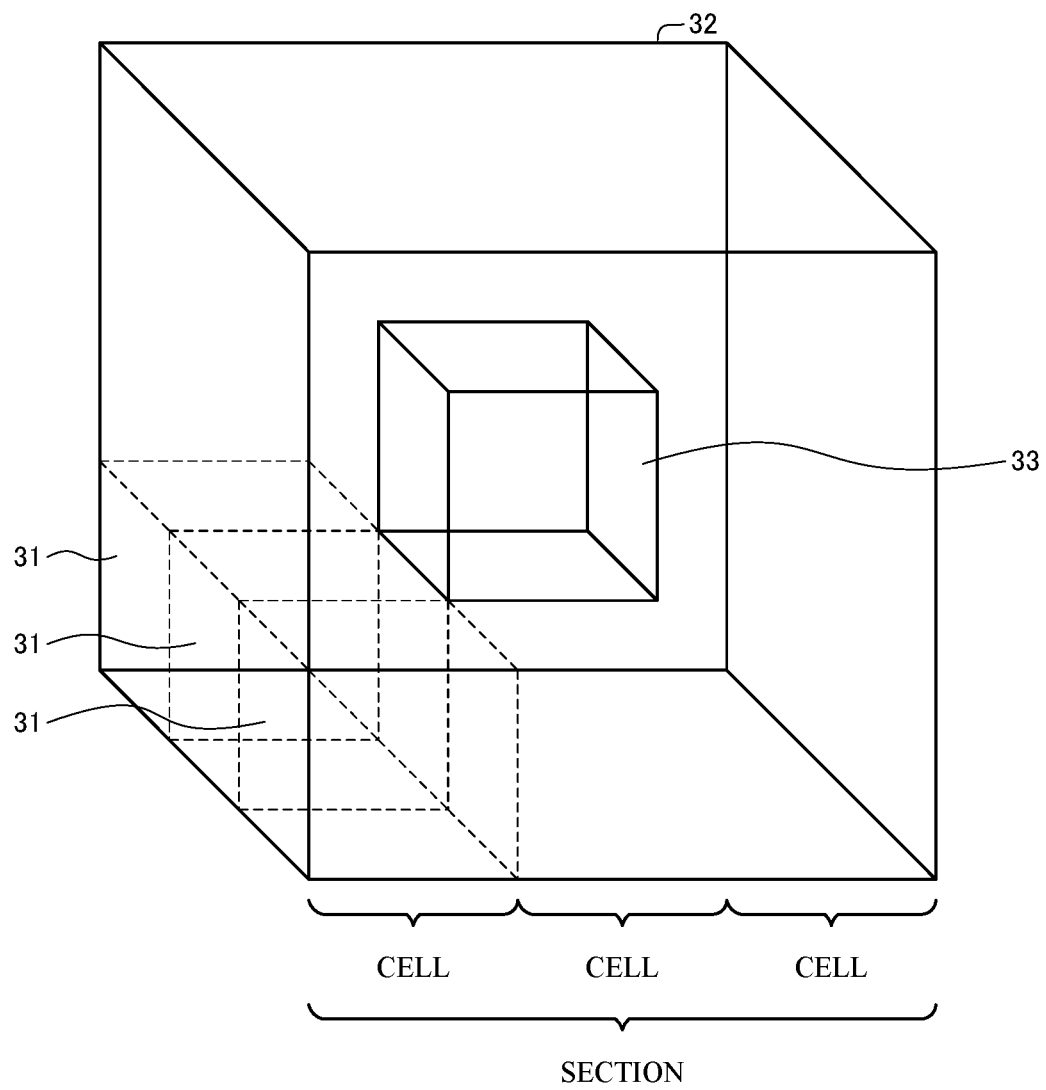
FIG. 3 is a diagram showing an example of a relation between a cell, a section and an important region.
Figure 4:
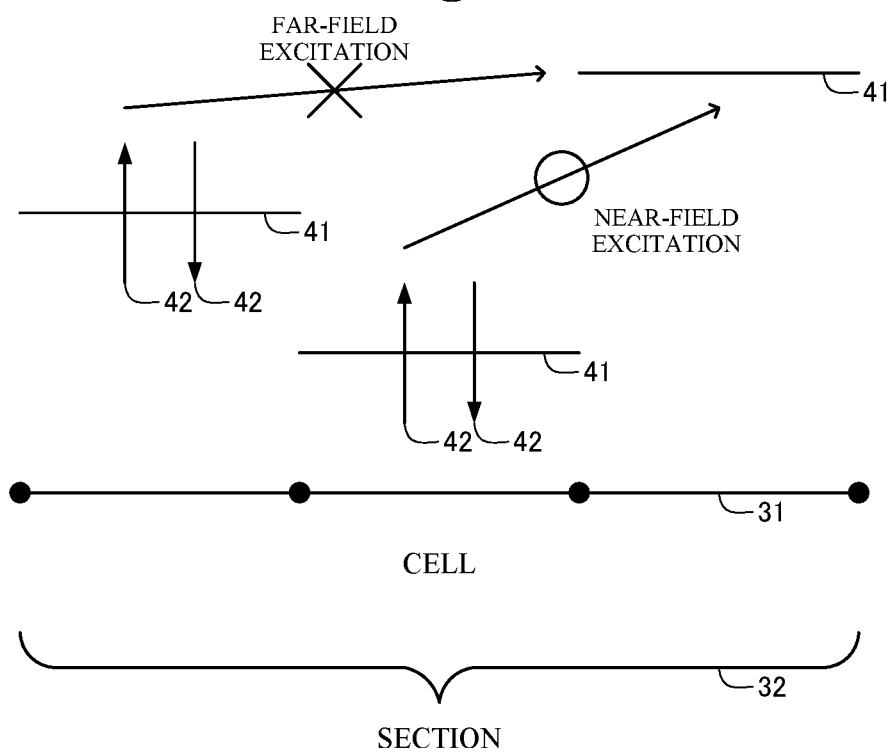
FIG. 4 is a diagram showing an example of inhibition of far-field excitation in generation of an electron configuration.
Figure 5:
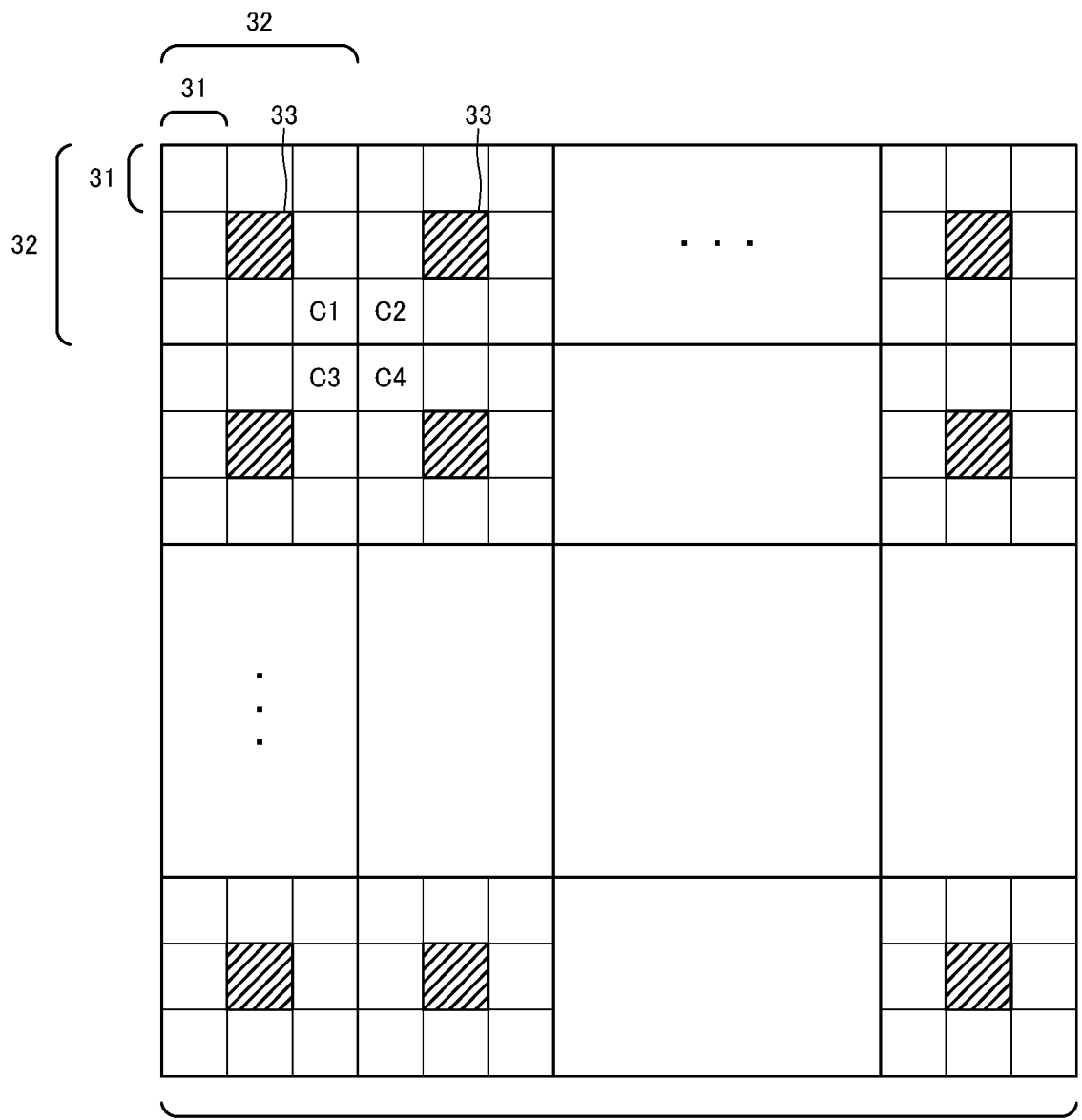
FIG. 5 is a diagram simply showing an example of a layer formed by a plurality of sections.
Figure 6:
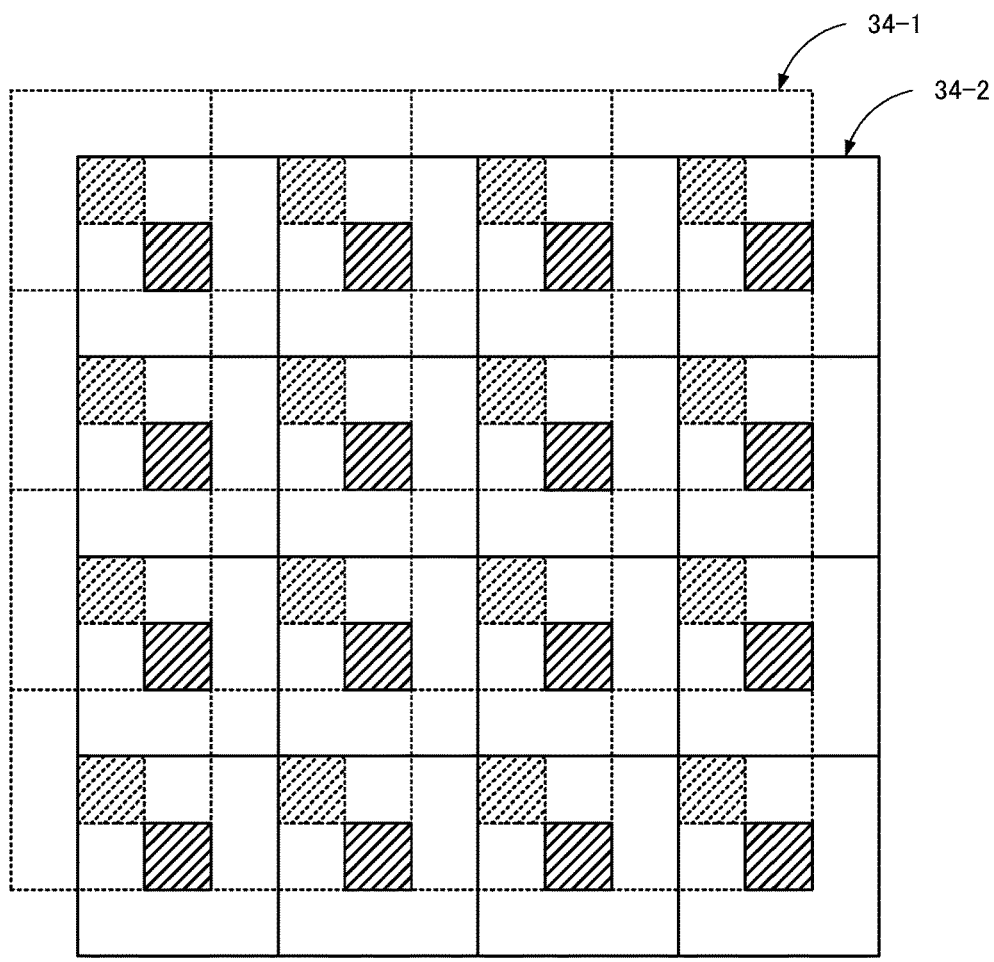
FIG. 6 is a diagram simply showing an example of a shifted layer.
Figure 7:
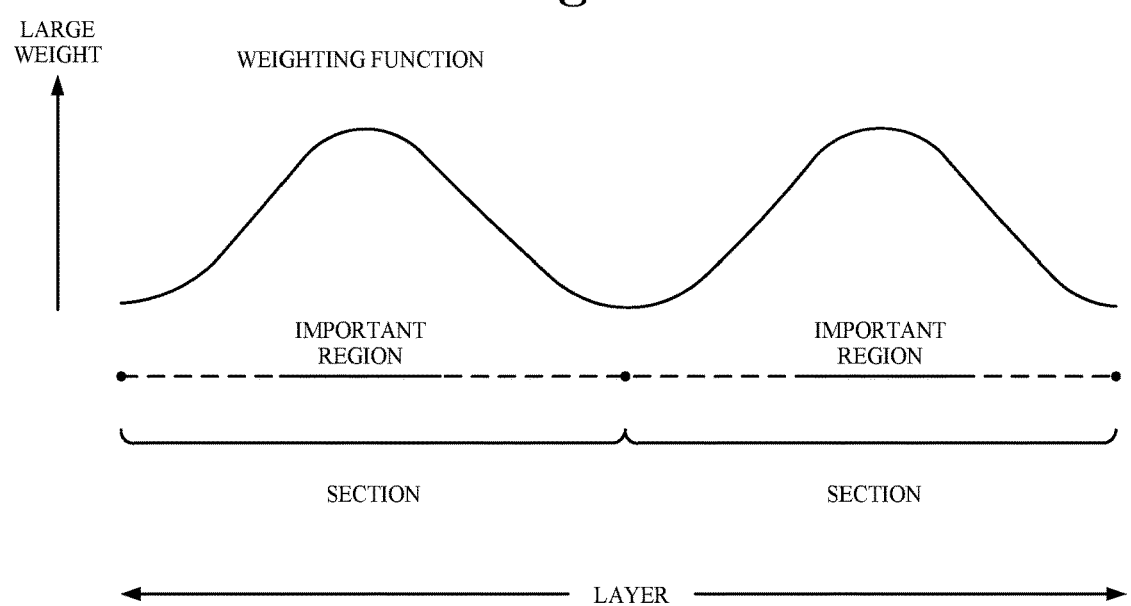
FIG. 7 is a diagram showing an example of a one-electron weighting function.
Figure 8:
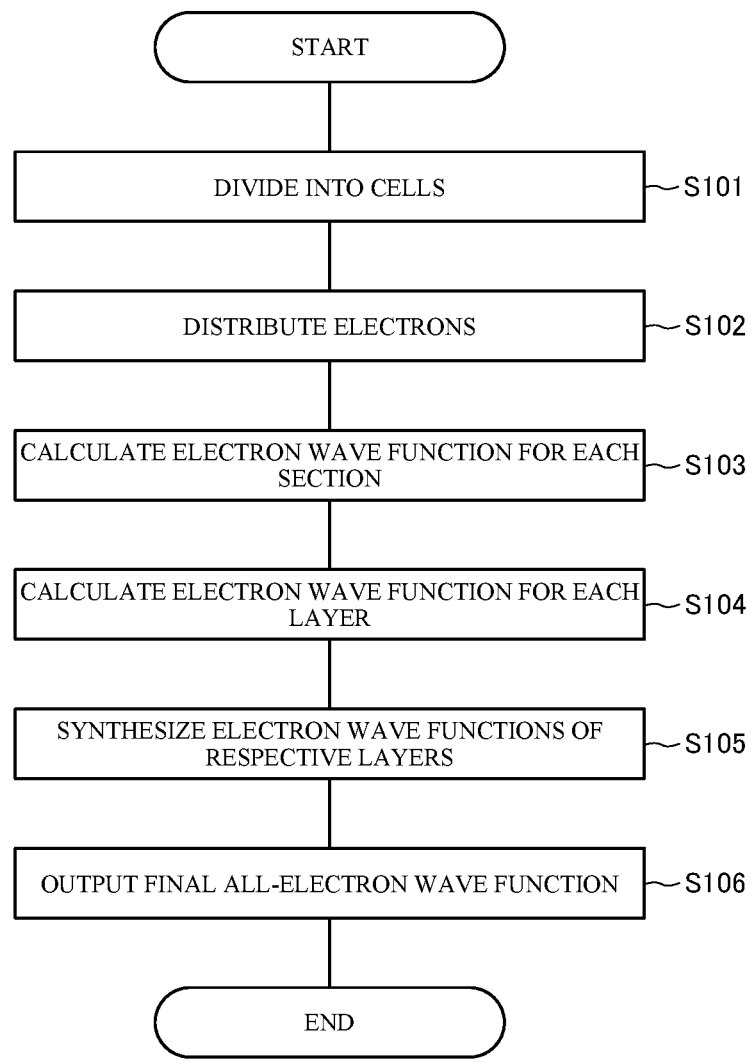
FIG. 8 is a flowchart showing an example of a process of the quantum chemistry calculation apparatus according to the first exemplary embodiment of the present invention.
Figure 9:
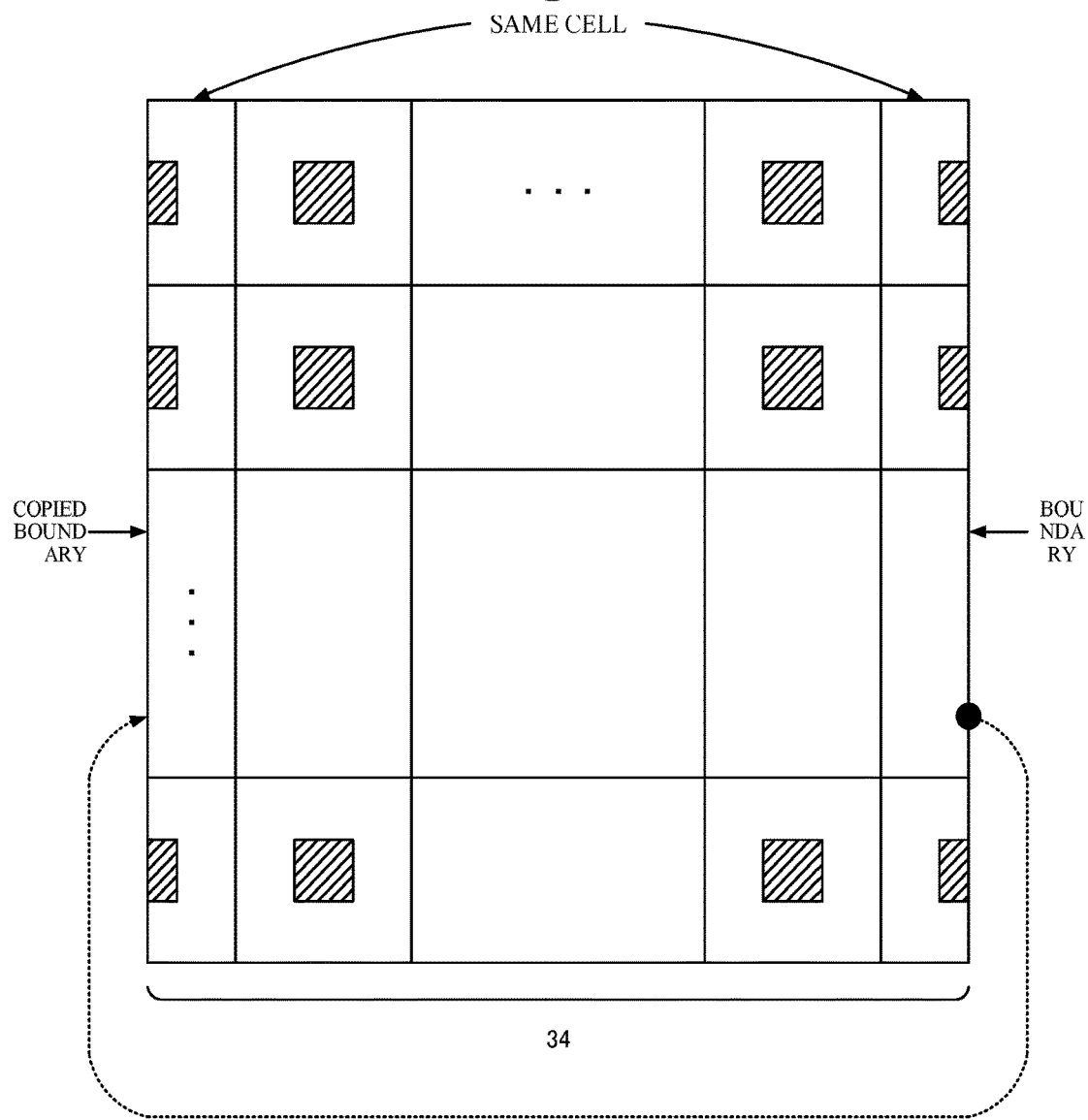
FIG. 9 is a diagram showing an example of realization of a periodic boundary condition.

A first exemplary embodiment of the present invention will be described with reference to FIGS. 1 to 9. FIG. 1 is a block diagram showing an example of a configuration of a quantum chemistry calculation apparatus 1. FIG. 2 is a diagram showing an example of dividing a space 3 including a system 2 (a molecular system, a crystal system, and the like) into cells 31. FIG. 3 is a diagram showing an example of a relation between the cell 31, the section 3, and an important region 33. FIG. 4 is a diagram showing an example of inhibition of far-field excitation in generation of an electron configuration. FIG. 5 is a diagram simply showing an example of a layer 34 formed by a plurality of sections 32. FIG. 6 is a diagram simply showing an example of a shifted layer 34 (for example, the section 32 is shifted). FIG. 7 is a diagram showing an example of a one-electron weighting function. FIG. 8 is a flowchart showing an example of a process of the quantum chemistry calculation apparatus 1. FIG. 9 is a diagram showing an example of realization of a periodic boundary condition;

In the first exemplary embodiment, the quantum chemistry calculation device 1 will be described. The quantum chemistry calculation device 1 calculates an all-electron wave function, which is a wave function of electrons included by a molecule system or a crystal system (in this exemplary embodiment, referred to as the system 2) that is a calculation target. As will be described later, the quantum chemistry calculation device 1 divides the space 3 including the system 2 that is a calculation target into a plurality of cells 31 on the basis of a given rule. Then, the quantum chemistry calculation apparatus 1 treats a section 32 formed by a plurality of cells 31 adjacent to each other as an isolated system, and calculates a local electron wave function including the surrounding environment for each section 32. After that, the quantum chemistry calculation device 1 calculates an all-electron wave function from the product of the local electron wave functions of the respective sections 32. An approximation that ignores an antisymmetry condition can be applied between isolated systems at long distances. Therefore, by treating the section 32 as an isolated system, it is possible to express an all-electron wave function as the product of the electron wave functions of the sections 32 isolated from each other. The quantum chemistry calculation apparatus 1 in this exemplary embodiment can calculate an all-electron wave function based on the result of local calculation by using the approximation as described above.

Further, the quantum chemistry calculation apparatus 1 calculates an electron wave function for each of the new sections 32 that the division points are regularly shifted, and calculates a new all-electron wave function from the product of the calculated electron wave functions. For example, the quantum chemistry calculation device 1 calculates an electron wave function for each section 32-1 to calculate a first all-electron wave function, and also calculates an electron wave function for each section 32-2 in which part of the included cells 31 is different from those of the section 32-1 to calculate a second all-electron wave function. The quantum chemistry calculation apparatus 1, for example, in the manner as described above, calculates all-electron wave functions of the respective sections 32 that are shifted a little from each other. Then, the quantum chemistry calculation apparatus 1 synthesizes the calculated all-electron wave functions by applying a predetermined weighting function. Thus, the quantum chemistry calculation apparatus 1 corrects an influence of division approximation (that is, an influence of considering the product of electron wave functions of the respective sections 32 as an all-electron wave function).

The quantum chemistry calculation apparatus 1 is an information processing apparatus that calculates an all-electron wave function of a molecular system or a crystal system (a system 2) that is a calculation target. For example, the quantum chemistry calculation apparatus 1 acquires a previously stored atomic coordinate 141, and calculates an all-electron wave function assuming that an atomic nucleus is fixed. With reference to FIG. 1, the quantum chemistry calculation apparatus 1 has, as major components, a communication I/F part 11, an operation input part 12, a screen display part 13, a storage part 14, and an arithmetic processing part 15.

The communication I/F part 11 is formed by a dedicated data communication circuit, and performs data communication with an external apparatus connected via a communication line.

The operation input part 12 is formed by an operation input device such as a keyboard and a mouse. The operation input part 12 detects operation by an operator who operates the quantum chemistry calculation apparatus 1, and outputs it to the arithmetic processing part 15.

The screen display part 13 is a screen display device such as an LCD (Liquid Crystal Display). The screen display part 13 displays various information such as an all-electron wave function 143 on a screen in accordance with an instruction by the arithmetic processing part 15.

The storage part 14 is a storage device such as a hard disk and a memory. The storage part 14 stores processing information necessary for various processing by the arithmetic processing part 15 and a program 144. In the program 144, a program that is loaded and executed to realize various processing parts is stored. The program 144 is previously loaded from an external apparatus (not shown in the drawings) or a storage medium (not shown in the drawings) via a data input/output function such as the communication I/F part 11 and stored into the storage part 14. Major information stored in the storage part 14 is, for example, the atomic coordinate 141, a basis function 142, the all-electron wave function 143, and so on. In the storage part 14, the result of processing by a cell dividing unit 151, an electron distributing unit 152, a section wave function calculating unit 153, a layer wave function calculating unit 154 or the like may be stored, for example, temporarily.

The atomic coordinate 141 shows the structure of the system 2 that is the target of calculation by the quantum chemistry calculation apparatus 1. For example, in the atomic coordinate 141, a list in which the type of an element constituting the system 2 and the three-dimensional coordinate of the element are combined to form one item. The coordinate may be defined by a z-matrix or the like. In other words, the atomic coordinate 141 may represent the structure of the system 2 by a bonding distance or a bonding angle between atoms, instead of a three-dimensional coordinate.

Thus, information showing the structure of the system 2 that is a calculation target is included in the atomic coordinate 141. The atomic coordinate 141 is, for example, previously loaded from an external apparatus (not shown in the drawings) or a storage medium (not shown) via a data input/output function such as the communication I/F part 11 and stored in the storage part 14.

The basis function 142 represents a well-known one-electron basis function defined for each element. In this exemplary embodiment, a basis function system included in the basis function 142 is not specifically limited. The basis function 142 is, for example, previously loaded from an external apparatus (not shown in the drawings) or a storage medium (not shown in the drawings) via a data input/output function such as the communication I/F part 11, and stored into the storage part 14.

The all-electron wave function 143 represents an all-electron wave function calculated by a layer synthesizing unit 155. An all-electron wave function represented by the all-electron wave function 143 can be, for example, transmitted to an external apparatus via the communication I/F part 11 or displayed by the screen display part 13.

The arithmetic processing part 15 has a microprocessor such as an MPU and a peripheral circuit thereof. The arithmetic processing part 15 loads the program 144 from the storage part 14 and executes it, thereby making the abovementioned hardware and the program 144 cooperate to realize various processing units. Major processing units realized by the arithmetic processing part 15 are a cell dividing unit 151 (a dividing unit), an electron distributing unit 152 (an electron distributing unit), a section wave function calculating unit 153 (an electron wave function calculating unit), a layer wave function calculating unit 154 (one of all-electron wave function calculating units), and a layer synthesizing unit 155 (one of the all-electron wave function calculating units). The arithmetic processing part 15 in this exemplary embodiment has, for example, a plurality of arithmetic units such as a plurality of processor cores and is configured to be able to execute parallel calculation as necessary.

The cell dividing unit 151 loads the atomic coordinate 141 corresponding to the system 2 that is a calculation target from the storage part 14. Subsequently, the cell dividing unit 151 divides a given space 3 including the structure of the system 2 represented by the atomic coordinate 141 into a plurality of cells 31 (small regions).

Each of the cells 31 into which the cell dividing unit 151 divides may have any shape. For example, the cell dividing unit 151 may define the cells 31 in the form of dividing molecular chains or define the cells 31 in the form of dividing the space 3 including the system 2 into an orthogonal equidistant grid. Moreover, the shape of the space 3 is defined indirectly in accordance with an important region 33 to be described later because the position of the important region 33 is defined.

For example, with reference to FIG. 2, the cell dividing unit 151 divides the space 3 including the system 2 into a plurality of cells 31 having a shape of an orthogonal equidistant grid. Thus, in the case of dividing the space 3 including the system 2 into a plurality of cells 31 having a shape of an orthogonal equidistant grid, the cell dividing unit 151 can automatically divide the space 3 at desired intervals due to the regularity. In this exemplary embodiment, the size of the cell 31 is not specifically limited. The cell dividing unit 151 may be configured to regulate the size of the cell 31 in accordance with the size of the system 2, or may be configured to use a cell 31 having a fixed size regardless of the size of the system 2. Moreover, in the case of defining the cells 31 in the form of dividing molecular chains, the cell dividing unit 151 manually specifies suitable division points (for example, the operator specifies via the operation input part 12) or automatically specifies. In this exemplary embodiment, a method for specifying division points is not specifically limited.

Thus, the cell dividing unit 151 divides a given space 3 including the structure of the system 2 into a plurality of cells 31 (small regions). After that, the cell dividing unit 151 transmits information representing the result of division to the electron distributing unit 152. As will be described later, a plurality of cells 31 (small regions) adjacent to each other obtained by division by the cell dividing unit 151 form a section 32 (a region). Therefore, it can be said that the cell dividing unit 151 divides the space 3 including the system 2 into a plurality of sections 32 (regions).

The electron distributing unit 152 distributes a-spin electrons and 8-spin electrons corresponding to the system 2 for each of the cells 31 on the basis of information received from the cell dividing unit 151. Alternatively, the electron distributing unit 152 distributes a-spin electrons and 8-spin electrons corresponding to the system 2 for each of the sections 32 (regions) surrounding the important region 33.

Now, the important region 33 (a specific region) and the section 32 will be described. The important region 33 is a portion that reflects the electron wave function of the important region 33 onto a final all-electron wave function with high weight. For example, the important region 33 is configured so that, when all the shifted layers 34 to be described later are stacked, a group of important regions 33 cover the system 2. That is, the important region 33 is formed so that the structure of the system 2 is not located outside the group of important regions 33. Thus, the important region 33 is defined in accordance with the structure of the system 2. In a case where the cells 31 are configured in the form of an orthogonal equidistant grid, the length of one side of the important region 33 is, for example, an integral multiple (for example, a single multiple) of the length of one side of the cell 31. Moreover, the section 32 is formed by a predetermined number of cells 31 adjacent to each other. However, the sections 32 are not overlapped. That is, each cell 31 belongs to only one section 32.

An example of the relation between the cells 31, the sections 32 and the important region 33 in a case where the cells 31 are formed in a shape of an orthogonal equidistant grid is shown in FIG. 3. With reference to FIG. 3, the section 32 is formed by twenty-seven cells 31 in total; length×width×height=3×3×3=27. The cell 31 located in the center of the section 32 overlaps the important region 33. Thus, the section 32 is formed so as to cover the important region 33. Moreover, the boundary of the important region 33 overlaps the boundaries of the cells 31 in a case where the number of the cells 31 of one side of the section 32 is an odd number. Meanwhile, the example shown by FIG. 3 is merely an example. The section 32 may be formed by eight cells 31 in total; length×width×height=2×2×2=8, or may be formed by cells 31 other than illustrated. In a case where the number of the cells 31 of one side of the section 32 is an even number, the boundary of the important region 33 overlaps a plane passing the center of the cell 31 and parallel to the boundary of the cell 31.

The above is the description of the important region 33 and the section 32.

As described above, the electron distributing unit 152 distributes electrons, for example, for each of the cells 31. For example, the electron distributing unit 152 loads the basis function 142 from the storage part 14, and calculates a molecular orbital by a previous method such as the Hartree Fock method in the cell 31. In this case, the electron distributing unit 152 can perform the calculation of molecular orbitals by parallel processing with the number of the cells 31 as the maximum parallel number. Because the calculation of a molecular orbital by the Hartree Fock method is well-known, a detailed description thereof will be omitted. Subsequently, the electron distributing unit 152 sorts the calculated molecular orbitals of the respective cells 31 by energy of the molecular orbitals (that is, rearranges the molecular orbitals in accordance with energy). Then, the electron distributing unit 152 arranges a-spin electrons and 8-spin electrons in order from the molecular orbital of small energy. Thus, the electron distributing unit 152 calculates the molecular orbitals of the respective cells 31, and distributes a-spin electrons and 8-spin electrons to the respective cells 31 on the basis of the calculated molecular orbitals. As a result of execution of such processing, the number of electrons distributed to each of the cells 31 is the total number of electrons distributed to the molecular orbital belonging to the cell 31.

Alternatively, the electron distributing unit 152 distributes electrons on the section 32 basis, instead of distributing electrons on the cell 31 basis. In the case of distributing electrons in the section 32 basis, the electron distributing unit 152 loads the basis function 142 from the storage part 14, and calculates a molecular orbital by a previous method such as the Hartree Fock method in the section 32. In this case, the electron distributing unit 152 can perform the calculation of molecular orbitals by parallel processing with the number of the sections 32 as the maximum parallel number. Because the calculation of a molecular orbital by the Hartree Fock method is well-known, a detailed description thereof will be omitted. Subsequently, the electron distributing unit 152 sorts the calculated molecular orbitals of the respective sections 32 by energy of the molecular orbitals (that is, rearranges the molecular orbitals in accordance with energy). Then, the electron distributing unit 152 arranges a-spin electrons and B-spin electrons in order from the molecular orbital of small energy. Thus, the electron distributing unit 152 calculates the molecular orbitals of the respective sections 32, and distributes a-spin electrons and B-spin electrons to the respective sections 32 on the basis of the calculated molecular orbitals. As a result of execution of such processing, the number of electrons distributed to the section 32 is the total number of electrons distributed to the molecular orbital belonging to the section 32.

Thus, the electron distributing unit 152 distributes a-spin electrons and B-spin electrons on the cell 31 basis or on the section 32 basis. After that, the electron distributing unit 152 transmits information including the result of the distribution to the section wave function calculating unit 153.

Herein, it may be arbitrarily set whether the electron distributing unit 152 distributes electrons on the cells 31 basis or distributes electrons on the section 32 basis. In a case where the electron distributing unit 152 distributes electrons on the section 32 basis, the section wave function calculating unit 153 to be described later uses the result of calculation of molecular orbitals performed by the electron distributing unit 152 as it is, and consequently, computational complexity can be reduced. On the other hand, in a case where the electron distributing unit 152 distributes electrons on the cell 31 basis, when calculating an electron wave function in a shifted section 32 to be described later, the section wave function calculating unit 153 can easily calculate the number of electrons belonging to the shifted section 32. This is because the number of electrons belonging to the section 32 is the total of the numbers of electrons distributed to the cells 31 configuring the section 32.

The section wave function calculating unit 153 calculates a local electron wave function (a many-electron wave function) for each section 32. For example, the section wave function calculating unit 153 loads the basis function 142 from the storage part 14 and calculates a local electron wave function by a previous method. In this case, the section wave function calculating unit 153 performs the calculation with the use of the number of atoms in the section 32 and the number of electrons in the section 32 distributed by the electron distributing unit 152. Herein, the section wave function calculating unit 153 can be configured to perform the calculation by parallel processing with the number of the sections 32 as the maximum parallel number. Moreover, in a case where the electron distributing unit 152 distributes electrons for each cell 31, the section wave function calculating unit 153 sums the numbers of electrons distributed to the cells 31 configuring the section 32 and considers the total as the number of the electrons in the section 32. Because the calculation is performed by a well-known method, a detailed description thereof will be omitted.

It is desired that the section wave function calculating unit 153 is configured to select a calculation method considering electron correlation such as the CI (configuration interaction) method and calculate the electron wave function. By selecting a calculation method considering electron correlation such as the CI method, it is possible to incorporate electron correlation into an all-electron wave function calculated by the layer wave function calculating unit 154 or the layer synthesizing unit 155 to be described later. For example, the section wave function calculating unit 153 calculates an electron wave function for each section 32 by the CISD (single and double excitations) method with single and double electron excitations.

As stated above, in a case where the electron distributing unit 152 calculates a molecular orbital for each section 32, the section wave function calculating unit 153 utilizes the result of calculation by the electron distributing unit 152 and thereby reducing computational complexity. Moreover, in a case where the electron distributing unit 152 calculates a molecular orbital on the cell 31 basis, the molecular orbitals of the adjacent cells 31 have small spatial overlap. Therefore, dependency between the cells is considered to be low, and an electron wave function is calculated as it is. In this case, by excluding far-field excitation as shown in FIG. 4 in the process of generating an electron configuration, it is also possible to reduce electron configuration to be incorporated into calculation. In other words, in the CI method, linear combination of configuration state functions (CSF) is used. By allowing only near-field excitation and forbidding far-field excitation when generating electron configuration of the derivation sources of the configuration state functions, it is possible to suppress the number of electron configurations and suppress computational complexity. FIG. 4 shows whether to forbid excitation of an electron 42 from a molecular orbital 41 and, for example, shows allowing excitation between the adjacent cells 31 as near-field excitation and forbidding excitation between the cells 31 that are not adjacent to each other as far-field excitation. FIG. 4 depicts in one dimension for ease of a description. A standard for distinguishing between near-field excitation and far-field excitation may be arbitrarily set; for example, excitation between the adjacent cells 31 is regarded as near-field excitation and the other is regarded as far-field excitation.

For example, in the above manner, the section wave function calculating unit 153 calculates an electron wave function for each section 32. Then, the section wave function calculating unit 153 transmits the calculated electron wave functions to the layer wave function calculation unit 154.

Now, let us consider a collection of the sections 32, which is referred to as the layer 34. FIG. 5 is a conceptual diagram of the layer 34 divided into an orthogonal equidistance grid. In FIG. 5, the layer 34 is shown in two dimension for the sake of simplicity. As shown in FIG. 5, the boundary of the section 32 is the boundary of the cell 31. However, the boundary of the section 32 can be the boundary of another cell 31. In other words, for example, although a cell C1 is located in the lower right of the section 32 located in the upper left of the sections 32 included by the layer 34 in FIG. 5, for example, the cell 31 located in the lower right of the section 32 may be a cell C2, C3 or C4. Thus, by shifting the section 32, it is possible to configure several types of layers 34. For example, FIG. 6 is a conceptual diagram of a shifted layer 34 when the cells 31 are divided by an orthogonal equidistance grid. FIG. 6 shows the layer 34 in two dimension for the sake of simplicity. With reference to FIG. 6, a layer 34-1 and a layer 34-2 that is shifted with respect to the layer 34-1.

As described above, the section 32 (the layer 34) to be the target of calculation by the section wave function calculating unit 153 can be shifted. Then, the section wave function calculating unit 153 also calculates an electron wave function for each shifted section 32. In this case, the section wave function calculating unit 153 instructs the electron distributing unit 152 to distribute electrons to the shifted sections 32 as necessary. For example, in this exemplary embodiment, the section 32 is shifted on the cell 31 basis so that the important region 33 is adjacent in the width, height and depth directions. Therefore, as the way to shift the section 32 (the number of layers 34 that can be generated by shifting), there are twenty-seven ways; 3×3×3=27.

In this exemplary embodiment, the section wave function calculating unit 153 calculates an electron wave function for each of the shifted sections 32 (layer 34). That is, in the case shown in FIG. 6, the section wave function calculating unit 153 calculates, for the layer 34-1, an electron wave function of each of the sections 32 corresponding to the layer 34-1 and also calculates, for the layer 34-2, an electron wave function of each of the sections corresponding to the layer 34-2. The section wave function calculating unit 153 performs such calculation for each layer 34. Therefore, for example, in a case where the section 32 is shifted on the cell 31 basis so that the important region 33 is adjacent in the width, height and depth directions as stated above, the section wave function calculating unit 153 performs the calculation of an electron wave function for each of the sections 32 twenty-seven times, for example. Meanwhile, the section wave function calculating unit 153 may be configured to perform the calculation in parallel processing with the number of layers as the maximum parallel number.

As stated above, in a case where the electron distributing unit 152 distributes electrons on the cell 31 basis, there is no need to cause the electron distributing unit 152 to operate again when calculating an electron wave function for each of the shifted sections 32. This is because, as stated above, the number of electrons belonging to the section 32 is the total of the numbers of electrons distributed to the cells 31 configuring the section 32.

The layer wave function calculating unit 154 calculates an all-electron wave function by multiplying the electron wave functions of the respective sections 32 received from the section wave function calculating unit 153. As stated above, for example, the section wave function calculating unit 153 performs calculation of an electron wave function of each of the sections 32 twenty-seven times. Therefore, the layer wave function calculating unit 154 calculates twenty-seven all-electron wave functions for each layer 34. After that, the layer wave function calculating unit 154 transmits information showing the result of the calculation to the layer synthesizing unit 155.

The layer synthesizing unit 155 synthesizes all-electron wave functions of the respective layers 34 calculated by the layer wave function calculating unit 154. For example, the layer synthesizing unit 155 synthesizes all-electron wave functions with the use of a predetermined weighting function. Thus, the layer synthesizing unit 155 calculates a final all-electron wave function. Then, the layer synthesizing unit 155 stores the calculated final all-electron wave function into the all-electron wave function 143 of the storage part 14. Moreover, the layer synthesizing unit 155 can transmit the calculated final all-electron wave function to an external apparatus via the communication I/F part 11 or cause the screen display part 13 to display it.

To be specific, for example, the layer synthesizing unit 155 multiplies a many-electron weighting function F1 as shown by the following equation 1 by each of the all-electron wave functions of the respective layers 34. Then, the layer synthesizing unit 155 finds the sum of the results of the multiplication. For example, the layer synthesizing unit 155 thus finds the sum of the results of multiplication of the many-electron weighting function F1, and synthesizes the all-electron wave functions of the respective layers 34 to calculate a final all-electron wave function.

$$F_l(x_1, x_2, \ldots, x_N) = \prod_{i=1}^{N} f(x_i - r_l) \quad \text{[Equation 1]}$$

In the equation 1, f denotes a one-electron weighting function (shown in FIG. 7). Moreover, N denotes the number of all electrons, i denotes an index of an electron, l denotes an index of a layer, $x_i$ denotes an $i^{th}$ electron coordinate, and $r_l$ denotes a parallel movement amount (a shift) of an $l^{th}$ layer.

FIG. 7 shows an example of the one-electron weighting function in the equation 1. With reference to FIG. 7, the local maximum of the one-electron weighting function exists in the important region 33. Moreover, the value of the weighting function is 0 or more at all times. For example, the one-electron weighting function in this exemplary embodiment is a trigonometric function having the local maximum in the important region 33 and the local minimum value of 0. The sum of the one-electron weighting functions of all the layers 34 needs to be 1 in all the regions. For example, a part corresponding to the cell C1 of FIG. 5 is not the important region 33 in the layer 34 shown in FIG. 5, but this part is the important region 33, for example, in the layer 34 shifted to the lower right as shown in FIG. 6. Thus, whether a region (for example, a position corresponding to the cell C1) is the important region 33 or not, how far the region is from the important region 33, and so on change depending on the degree of shift of the layer 34. That is, with respect to a certain region, a value shown by the one-electron weighting function varies depending on the degree of shift of the layer 34. In this exemplary embodiment, the sum of the values indicated by the one-electron weighting functions for an identical position (for example, the position of the cell C1) in the respective layers 34 shifted from each other is 1.

The above is an example of the configuration of the quantum chemistry calculation apparatus 1. Subsequently, with reference to FIG. 8, an example of processing of the quantum chemistry calculation apparatus 1 will be described.

With reference to FIG. 8, the cell dividing unit 151 of the quantum chemistry calculation device 1 loads the atomic coordinate 141 corresponding to the system 2 that is a calculation target from the storage part 14. Then, the cell dividing unit 151 divides a given space 3 including the structure of the system 2 represented by the atomic coordinate 141 into a plurality of cells 31 (step S101).

The electron distributing unit 152 distributes a-spin electrons and 8-spin electros in units of the cell 31 obtained by division by the cell dividing unit 151 or in units of the section 32 surrounding the important region 33 (step S102). For example, the electron distributing unit 152 loads the basis function 142 from the storage part 14 and calculates a molecular orbital by a previous method such as the Hartree Fock method in the cell 31 or in the section 32. Subsequently, the electron distributing unit 152 sorts the calculated molecular orbitals by energy of the molecular orbitals, and arranges a-spin electrons and 8-spin electrons in order from the molecular orbital of small energy. For example, by such processing, the electron distributing unit 152 distributes a-spin electrons and 8-spin electrons on the cell 31 basis or on the section 32 basis. Meanwhile, the calculation of the molecular orbitals may be performed in parallel.

The section wave function calculating unit 153 calculates a local electron wave function for each of the sections 32 on the basis of the result of distribution by the electron distributing unit 152 (step S103). For example, the section wave function calculating unit 153 loads the basis function 142 from the storage part 14 and calculates a local electron wave function by a previous method. In the calculation, the section wave function calculating unit 153 performs the calculation with the use of the number of the atoms in the section 32 and the number of the electrons in the section 32 distributed by the electron distributing unit 152. Moreover, the section wave function calculating unit 153 performs the calculation of an electron wave function of each of the sections 32 for each shifted layer 34. The calculation of electron wave functions for the respective sections 32 and the calculation for the respective layers 34 may be performed in parallel.

The layer wave function calculating unit 154 calculates an all-electron wave function by multiplying the electron wave functions of the respective sections 32 (step S104). As stated above, the section wave function calculating unit 153 performs the calculation of electron wave functions of the respective sections 32 for each of the shifted layers 34. Therefore, the layer wave function calculating unit 154 calculates an all-electron wave function according to the number of the shifted layers 34.

The layer synthesizing unit 155 synthesizes the all-electron wave functions calculated by the layer wave function calculating unit 154 to calculate a final all-electron wave function (step S105). The layer synthesizing unit 155, for example, synthesizes the electron wave functions with the use of the multi-electron weighting function F1 as shown by the equation 1. After that, the layer synthesizing unit 155 outputs the final all-electron wave function that is the result of the synthesis (step S106). That is, the layer synthesizing unit 155 stores the calculated final all-electron wave function into the storage part 14, transmits to an external apparatus via the communication I/F part 11, or causes the screen display part 13 to display.

Thus, the quantum chemistry calculation apparatus 1 according to this exemplary embodiment has the cell dividing unit 151, the section wave function calculating unit 153, and the layer wave function calculating unit 154. Such a configuration allows the section wave function calculating unit 153 to treat the section 32 formed by a plurality of cells 31 obtained by division by the cell dividing unit 151 as an isolated system and calculate a local electron wave function for each section 32. Moreover, the layer wave function calculating unit 154 can calculate an all-electron wave function from the product of the local electron wave functions of the respective sections 32. An approximation that ignores an anticommutation relation can be applied between systems isolated at long distance. Therefore, by treating the section 32 as an isolated system, it is possible to represent an all-electron wave function as the product of the electron wave functions of the isolated sections 32. The quantum chemistry calculation device 1 according to this exemplary embodiment uses the approximation as described above, thereby allowing calculation of an all-electron wave function based on the local calculation result. Consequently, it is possible to suppress computational complexity.

Further, the quantum chemistry calculation apparatus 1 has the layer synthesizing unit 155, and the section wave function calculating unit 153 is configured to calculate an all-electron wave function for each of a plurality of sections 32 that are shifted a little from each other. Such a configuration allows the layer synthesizing unit 155 to synthesize the all-electron wave functions of the respective layers 34 that are shifted a little from each other calculated by the section wave function calculating unit 153 and the layer wave function calculating unit 154. Thus, the quantum chemistry calculation device 1 can correct an effect of division approximation (that is, an effect of regarding the product of the electron wave functions of the respective sections 32 as an all-electron wave function). That is, it is possible to perform calculation with higher accuracy.

Further, according to the quantum chemistry calculation apparatus 1 of this exemplary embodiment, the section wave function calculating unit 153 can use, for example, the CI method considering electron correlation when calculating a local wave function. As a result, it is possible to calculate an all-electron wave function considering electron correlation while suppressing computational complexity.

In a case where the system 2 is a crystal system, periodic boundaries can be realized by including the opposite cell 31 into the section 32. FIG. 9 shows a conceptual diagram of realization of periodic boundaries in a case where the cells 31 have a shape of an orthogonal equidistant grid. FIG. 9 depicts in two dimension for the sake of simplification. Thus, it is possible that the quantum chemistry calculation apparatus 1 calculates an all-electron wave function of a crystal system by setting the surrounding environment at the time of calculation of local wave functions in each divided system in consideration of periodic boundaries.

Further, when the electron distributing unit 152 distributes electrons, and when the section wave function calculating unit 153 calculates electron wave functions of the respective sections 32, it is desirable to consider an influence of nearby electric charges that acts a relatively long distance. However, in order to consider an influence of nearby electric charges, nearby electron density (electron wave function) is needed, which cannot be determined unless the electron wave function of a target section (for example, the section 32 adjacent to the section 32 that is a calculation target) is not obtained. That is, when the electron distributing unit 152 distributes electrons, and when the section wave function calculating unit 153 calculates electron wave functions of the respective sections 32, for example, it is desirable that the electron wave function of the section 32 adjacent to the section 32 that is a calculation target has been calculated. In order to cope with such a situation, the quantum chemistry calculation apparatus 1 can be configured to, so as to be self-consistent, perform repeated calculation, which is calculating an all-electron wave function, feeding it back, obtaining a neighbor charge and recalculating. By thus configuring the quantum chemistry calculation apparatus 1 to repeatedly calculate an all-electron wave function, the quantum chemistry calculation apparatus 1 can perform calculation with higher precision. Meanwhile, the repeated calculation may be any number of times by the quantum chemistry calculation device 1 may be any number.

Second Exemplary Embodiment

Next, with reference to FIG. 10, a second exemplary embodiment of the present invention will be described. In the second exemplary embodiment, the outline of the configuration of a calculation apparatus 5 will be described.

Figure 10:
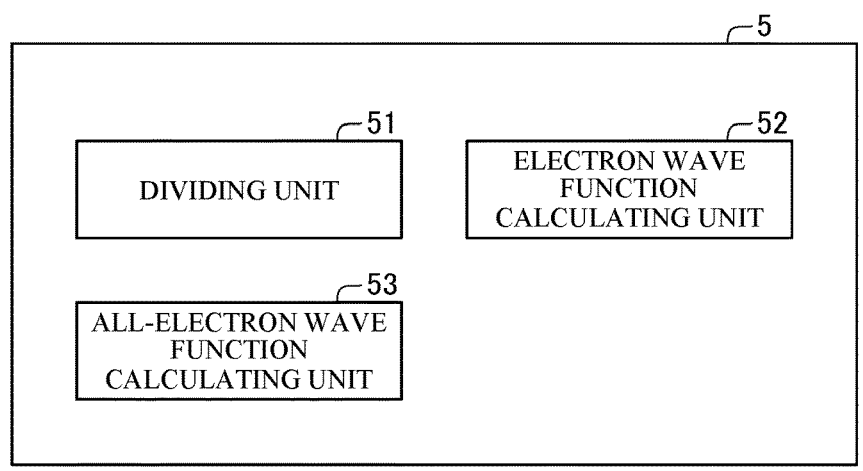
FIG. 10 is a block diagram showing an example of a configuration of a calculation device according to a second exemplary embodiment of the present invention.

With reference to FIG. 10, the calculation apparatus 5 has a dividing unit 51, an electron wave function calculating unit 52, and an all-electron wave function calculating unit 53. For example, the calculation apparatus 5 has an arithmetic device and a storage device, which are not shown in the drawings, and executes a program stored in the storage device to realize the units described above.

The dividing unit 51 divides a given space including a substance that is a calculation target into a plurality of regions.

The electron wave function calculating unit 52 calculates an electron wave function for each of the regions obtained by division by the dividing unit 51.

The all-electron wave function calculating unit 53 calculates an all-electron wave function by multiplying electron wave functions of the respective regions calculated by the electron wave function calculating unit 52.

Thus, the calculation apparatus 5 in this exemplary embodiment has the dividing unit 51, the electron wave function calculating unit 52, and the all-electron wave function calculating unit 53. Such a configuration allows the electron wave function calculating unit 52 of the calculation apparatus 5 to treat each of the regions obtained by division by the dividing unit 51 as an isolated system and calculate a local electron wave function for each of the regions. Moreover, the all-electron wave function calculating unit 53 can calculate an all-electron wave function from the product of the local electron wave functions of the respective regions calculated by the electron wave function calculating unit 52. An approximation that ignores an anticommutation relation can be applied between isolated systems at long distances. Therefore, by treating a region as an isolated system, it is possible to represent an all-electron wave function as the product of electron wave functions of isolated regions. The calculation apparatus 5 in this exemplary embodiment uses the approximation as stated above to be able to suppress computational complexity at the time of calculation of an all-electron wave function.

Further, the calculation apparatus 5 described above can be realized by installation of a predetermined program into the calculation apparatus 5. To be specific, a program as another aspect of the present invention is a program including instructions for causing an information processing apparatus to realize a dividing unit 51, an electron wave function calculating unit 52, and an all-electron wave function calculating unit 53. The dividing unit 51 is configured to divide a given space including a substance that is a calculation target into a plurality of regions. The electron wave function calculating unit 52 is configured to calculate an electron wave function for each of the regions obtained by division by the dividing unit 51. The all-electron wave function calculating unit 53 is configured to calculate an all-electron wave function by multiplying the electron wave functions of the respective regions calculated by the electron wave function calculating unit 52.

Further, a calculation method executed by the calculation apparatus 5 described above is a method including that an information processing apparatus divides a given space including a substance that is a calculation target into a plurality of regions, calculates an electron wave function for each of the regions, and calculates an all-electron wave function by multiplying the electron wave functions of the respective calculated regions.

An invention of a program or a calculation method that has the abovementioned configuration can also achieve the object of the present invention because has the same actions as the calculation apparatus 5.

<Supplementary Notes>

The whole or part of the exemplary embodiments disclosed above can be described as the following supplementary notes. The outline of a calculation apparatus and so on according to the present invention will be described below. However, the present invention is not limited to the following configurations.

(Supplementary Note 1)

A calculation apparatus comprising:

a dividing unit configured to divide a predetermined space including a substance of a calculation target into a plurality of regions;

an electron wave function calculating unit configured to calculate an electron wave function for each of the regions obtained by the dividing by the dividing unit; and an all-electron wave function calculating unit configured to calculate an all-electron wave function by multiplying electron wave functions of the respective regions calculated by the electron wave function calculating unit.

(Supplementary Note 2)

The calculation apparatus according to Supplementary Note 1, wherein:

the electron wave function calculating unit is configured to calculate an electron wave function for each of first regions, and also calculate an electron wave function for each of second regions formed by shifting the first regions in a state that the second regions partially overlap the first regions; and the all-electron wave function calculating unit is configured to calculate a first all-electron wave function by multiplying electron wave functions of the respective first regions, also calculate a second all-electron function by multiplying electron wave functions of the respective second regions, and synthesize the calculated first all-electron wave function with the calculated second all-electron wave function.

(Supplementary Note 3)

The calculation apparatus according to Supplementary Note 2, wherein:

the dividing unit is configured to divide a predetermined space including a substance of a calculation target into small regions that are smaller than the regions, and each of the regions is formed by adjacent ones of the small regions; and the small region of the second region corresponding to the small region of the first region is shifted to a position that is different from a position of the small region of the first region.

(Supplementary Note 4)

The calculation apparatus according to Supplementary Note 3, comprising an electron distributing unit configured to distribute electrons to each of the regions or each of the small regions, wherein the electron wave function calculating unit is configured to calculate an electron wave function by using a number of the electrons distributed by the electron distributing unit.

(Supplementary Note 4-1)

The calculation apparatus according to Supplementary Note 4, wherein the electron wave function calculating unit is configured to calculate an electron wave function by applying a predetermined calculation method considering electron correlation and, in a process of generating electron configuration at a time of calculating an electron wave function, forbid excitation determined as far-field excitation on a basis of a predetermined standard.

(Supplementary Note 5)

The calculation apparatus according to Supplementary Note 4, wherein the electron distributing unit is configured to calculate molecular orbitals in the regions or the small regions in parallel for the respective regions or the respective small regions, and distribute electrons to the regions or the small regions on a basis of the calculated molecular orbitals.

(Supplementary Note 6)

The calculation apparatus according to any of Supplementary Notes 3 to 5, wherein the dividing unit is configured to consider the small region located at one of boundaries of the region and the small region located at other of the boundaries as same small regions, and set the boundaries of the region as periodic boundaries.

(Supplementary Note 7)

The calculation apparatus according to any of Supplementary Notes 2 to 6, wherein:

a specific region of the regions is a region in which an electron wave function calculated by the electron wave function calculating unit is reflected with higher weight than in a region other than the specific region of the regions; and the all-electron wave function calculating unit is configured to synthesize the first all-electron wave function with the second all-electron wave function by using a weight function that is a function having a local maximum in the specific region.

(Supplementary Note 7-1)

The calculation apparatus according to Supplementary Note 7, wherein the important region is formed in a position according to a structure of the substance of the calculation target.

(Supplementary Note 8)

The calculation apparatus according to any of Supplementary Notes 2 to 7, wherein the all-electron wave function calculating unit is configured to perform calculation of the first all-electron wave function and calculation of the second all-electron wave function in parallel.

(Supplementary Note 9)

A calculation method executed by an information processing apparatus, comprising:

dividing a predetermined space including a substance of a calculation target into a plurality of regions;

calculating an electron wave function for each of the regions obtained by the dividing; and calculating an all-electron wave function by multiplying calculated electron wave functions of the respective regions.

(Supplementary Note 10)

The calculation method according to Supplementary Note 9, comprising:

calculating an electron wave function for each of first regions, and also calculating an electron wave function for each of second regions formed by shifting the first regions in a state that the second regions partially overlap the first regions; and calculating a first all-electron wave function by multiplying electron wave functions of the respective first regions, also calculating a second all-electron function by multiplying electron wave functions of the respective second regions, and synthesizing the calculated first all-electron wave function with the calculated second all-electron wave function.

(Supplementary Note 11)

The calculation method according to Supplementary Note 10, wherein:

a predetermined space including a substance of a calculation target is divided into small regions that are smaller than the regions, and each of the regions is formed by adjacent ones of the small regions; and the small region of the second region corresponding to the small region of the first region is shifted to a position that is different from a position of the small region of the first region.

(Supplementary Note 12)

The calculation method according to Supplementary Note 11, wherein:

distributing electrons to each of the regions or each of the small regions; and calculating an electron wave function by using a number of the electrons distributed by the electron distributing unit.

(Supplementary Note 13)

The calculation method according to Supplementary Note 12, comprising:

calculating molecular orbitals in the regions or the small regions in parallel for the respective regions or the respective small regions, and distributing electrons to the regions or the small regions on a basis of the calculated molecular orbitals.

(Supplementary Note 14)

The calculation method according to Supplementary Note 11, comprising:

considering the small region located at one of boundaries of the region and the small region located at other of the boundaries as same small regions, and set the boundaries of the region as periodic boundaries.

(Supplementary Note 15)

A non-transitory computer-readable medium storing a program comprising instructions for causing an information processing apparatus to realize:

a dividing unit configured to divide a predetermined space including a substance of a calculation target into a plurality of regions;

an electron wave function calculating unit configured to calculate an electron wave function for each of the regions obtained by the dividing by the dividing unit; and an all-electron wave function calculating unit configured to calculate an all-electron wave function by multiplying electron wave functions of the respective regions calculated by the electron wave function calculating unit.

(Supplementary Note 16)

The non-transitory computer-readable medium storing the program according to Supplementary Note 15, wherein:

the electron wave function calculating unit is configured to calculate an electron wave function for each of first regions, and also calculate an electron wave function for each of second regions formed by shifting the first regions in a state that the second regions partially overlap the first regions; and the all-electron wave function calculating unit is configured to calculate a first all-electron wave function by multiplying electron wave functions of the respective first regions, also calculate a second all-electron function by multiplying electron wave functions of the respective second regions, and synthesize the calculated first all-electron wave function with the calculated second all-electron wave function.

(Supplementary Note 17)

The non-transitory computer-readable medium storing the program according to Supplementary Note 16, wherein:

the dividing unit is configured to divide a predetermined space including a substance of a calculation target into small regions that are smaller than the regions, and each of the regions is formed by adjacent ones of the small regions; and the small region of the second region corresponding to the small region of the first region is shifted to a position that is different from a position of the small region of the first region.

(Supplementary Note 18)

The non-transitory computer-readable medium storing the program according to Supplementary Note 17, wherein:

an electron distributing unit configured to distribute electrons to each of the regions or each of the small regions is included; and the electron wave function calculating unit is configured to calculate an electron wave function by using a number of the electrons distributed by the electron distributing unit.

(Supplementary Note 19)

The non-transitory computer-readable medium storing the program according to Supplementary Note 18, wherein the electron distributing unit is configured to calculate molecular orbitals in the regions or the small regions in parallel for the respective regions or the respective small regions, and distribute electrons to the regions or the small regions on a basis of the calculated molecular orbitals.

(Supplementary Note 20)

The non-transitory computer-readable medium storing the program according to Supplementary Note 17, wherein the dividing unit is configured to consider the small region located at one of boundaries of the region and the small region located at other of the boundaries as same small regions, and set the boundaries of the region as periodic boundaries.

The program described in the exemplary embodiments and supplementary notes is stored in a storage device or a recorded on a computer-readable recording medium. For example, the recording medium is a portable medium such as a flexible disk, an optical disk, a magneto-optical disk and a semiconductor memory.

Although the present invention has been described above with reference to the exemplary embodiment, the present invention is not limited to the exemplary embodiments. The configurations and details of the present invention can be changed in various manners that can be understood by one skilled in the art.

DESCRIPTION OF REFERENCE NUMERALS

1 quantum chemistry calculation apparatus
11 communication I/F part
12 operation input part
13 screen display part
14 storage part
141 atomic coordinate
142 basis function
143 all-electron wave function
144 program
15 arithmetic processing part
151 cell dividing unit
152 electron distributing unit
153 section wave function calculating unit
154 layer wave function calculating unit
155 layer synthesizing unit 2 system
3 space
31 cell
32 section
33 important region
34 layer
41 molecular orbital
42 electron
5 calculation apparatus
51 dividing unit
52 electron wave function calculating unit
53 all-electron wave function calculating unit

The invention claimed is:

1. A calculation apparatus comprising:
a dividing unit configured to divide a predetermined space including a substance of a calculation target into a plurality of regions;
an electron wave function calculating unit configured to calculate an electron wave function for each of the regions obtained by the dividing by the dividing unit; and
an all-electron wave function calculating unit configured to calculate an all-electron wave function by multiplying electron wave functions of the respective regions calculated by the electron wave function calculating unit.

2. The calculation apparatus according to claim 1, wherein:
the electron wave function calculating unit is configured to calculate an electron wave function for each of first regions, and also calculate an electron wave function for each of second regions formed by shifting the first regions in a state that the second regions partially overlap the first regions; and
the all-electron wave function calculating unit is configured to calculate a first all-electron wave function by multiplying electron wave functions of the respective first regions, also calculate a second all-electron function by multiplying electron wave functions of the respective second regions, and synthesize the calculated first all-electron wave function with the calculated second all-electron wave function.

3. The calculation apparatus according to claim 2, wherein:
the dividing unit is configured to divide a predetermined space including a substance of a calculation target into small regions that are smaller than the regions, and each of the regions is formed by adjacent ones of the small regions; and
the small region of the second region corresponding to the small region of the first region is shifted to a position that is different from a position of the small region of the first region.

4. The calculation apparatus according to claim 3, comprising an electron distributing unit configured to distribute electrons to each of the regions or each of the small regions,
wherein the electron wave function calculating unit is configured to calculate an electron wave function by using a number of the electrons distributed by the electron distributing unit.

5. The calculation apparatus according to claim 4,
wherein the electron distributing unit is configured to calculate molecular orbitals in the regions or the small regions in parallel for the respective regions or the respective small regions, and distribute electrons to the regions or the small regions on a basis of the calculated molecular orbitals.

6. The calculation apparatus according to claim 3,
wherein the dividing unit is configured to consider the small region located at one of boundaries of the region and the small region located at other of the boundaries as same small regions, and set the boundaries of the region as periodic boundaries.

7. The calculation apparatus according to claim 2, wherein:
a specific region of the regions is a region in which an electron wave function calculated by the electron wave function calculating unit is reflected with higher weight than in a region other than the specific region of the regions; and
the all-electron wave function calculating unit is configured to synthesize the first all-electron wave function with the second all-electron wave function by using a weight function that is a function having a local maximum in the specific region.

8. The calculation apparatus according to claim 2,
wherein the all-electron wave function calculating unit is configured to perform calculation of the first all-electron wave function and calculation of the second all-electron wave function in parallel.

9. A calculation method executed by an information processing apparatus, comprising:
dividing a predetermined space including a substance of a calculation target into a plurality of regions;
calculating an electron wave function for each of the regions obtained by the dividing; and
calculating an all-electron wave function by multiplying calculated electron wave functions of the respective regions.

10. The calculation method according to claim 9, comprising:
calculating an electron wave function for each of first regions, and also calculating an electron wave function for each of second regions formed by shifting the first regions in a state that the second regions partially overlap the first regions; and
calculating a first all-electron wave function by multiplying electron wave functions of the respective first regions, also calculating a second all-electron function by multiplying electron wave functions of the respective second regions, and synthesizing the calculated first all-electron wave function with the calculated second all-electron wave function.

11. The calculation method according to claim 10, wherein:
a predetermined space including a substance of a calculation target is divided into small regions that are smaller than the regions, and each of the regions is formed by adjacent ones of the small regions; and
the small region of the second region corresponding to the small region of the first region is shifted to a position that is different from a position of the small region of the first region.

12. The calculation method according to claim 11, comprising:
distributing electrons to each of the regions or each of the small regions; and
calculating an electron wave function by using a number of the electrons distributed by the electron distributing unit.

13. The calculation method according to claim 12, comprising:
calculating molecular orbitals in the regions or the small regions in parallel for the respective regions or the respective small regions, and distributing electrons to the regions or the small regions on a basis of the calculated molecular orbitals.

14. The calculation method according to claim 11, comprising:
considering the small region located at one of boundaries of the region and the small region located at other of the boundaries as same small regions, and set the boundaries of the region as periodic boundaries.

15. A non-transitory computer-readable medium storing a program comprising instructions for causing an information processing apparatus to realize:
a dividing unit configured to divide a predetermined space including a substance of a calculation target into a plurality of regions;
an electron wave function calculating unit configured to calculate an electron wave function for each of the regions obtained by the dividing by the dividing unit; and
an all-electron wave function calculating unit configured to calculate an all-electron wave function by multiplying electron wave functions of the respective regions calculated by the electron wave function calculating unit.

16. The non-transitory computer-readable medium storing the program according to claim 15, wherein:
the electron wave function calculating unit is configured to calculate an electron wave function for each of first regions, and also calculate an electron wave function for each of second regions formed by shifting the first regions in a state that the second regions partially overlap the first regions; and
the all-electron wave function calculating unit is configured to calculate a first all-electron wave function by multiplying electron wave functions of the respective first regions, also calculate a second all-electron function by multiplying electron wave functions of the respective second regions, and synthesize the calculated first all-electron wave function with the calculated second all-electron wave function.

17. The non-transitory computer-readable medium storing the program according to claim 16, wherein:
the dividing unit is configured to divide a predetermined space including a substance of a calculation target into small regions that are smaller than the regions, and each of the regions is formed by adjacent ones of the small regions; and
the small region of the second region corresponding to the small region of the first region is shifted to a position that is different from a position of the small region of the first region.

18. The non-transitory computer-readable medium storing the program according to claim 17, wherein:
an electron distributing unit configured to distribute electrons to each of the regions or each of the small regions is included; and
the electron wave function calculating unit is configured to calculate an electron wave function by using a number of the electrons distributed by the electron distributing unit.

19. The non-transitory computer-readable medium storing the program according to claim 18,
wherein the electron distributing unit is configured to calculate molecular orbitals in the regions or the small regions in parallel for the respective regions or the respective small regions, and distribute electrons to the regions or the small regions on a basis of the calculated molecular orbitals.

20. The non-transitory computer-readable medium storing the program according to claim 17,
wherein the dividing unit is configured to consider the small region located at one of boundaries of the region and the small region located at other of the boundaries as same small regions, and set the boundaries of the region as periodic boundaries.

* * * * *